United States Patent [19]

Alvarado et al.

[11] Patent Number: 5,676,944
[45] Date of Patent: Oct. 14, 1997

[54] OCULAR THERAPY WITH HOMOLOGOUS MACROPHAGES

[75] Inventors: Jorge A. Alvarado, Kentfield; Collin G. Murphy, Berkeley; Johnnie L. Hu, Portola Valley, all of Calif.

[73] Assignee: The Regents of the University of California, Oakland, Calif.

[21] Appl. No.: 132,622

[22] Filed: Oct. 6, 1993

[51] Int. Cl.$^6$ ........................................ A61K 35/14
[52] U.S. Cl. .............................. 424/93.71; 424/93.7
[58] Field of Search ........................ 424/93 B, 85.1, 424/85.2, 85.4, 93.7, 93.71

[56] References Cited

U.S. PATENT DOCUMENTS

| | | | |
|---|---|---|---|
| 4,878,895 | 11/1989 | Klesius et al. | 604/49 |
| 5,260,059 | 11/1993 | Acott et al. | 424/94.67 |
| 5,324,508 | 6/1994 | Adelstein et al. | 424/85.1 |

FOREIGN PATENT DOCUMENTS

| | | |
|---|---|---|
| 5117160 | 5/1993 | Japan . |
| 5130853 | 5/1993 | Japan . |
| 5117060 | 5/1993 | Japan . |

OTHER PUBLICATIONS

Tripathi et al., Invest Opthalmol. Vis Sci 34(8): 2562–2568 (Jul. 1993).
Wakefield et al., Cytokine (Philadelphia) 4(1): 1–5 (1992).
Gillies, Aust N. Z. J. Opthalmol. 19(4): 299–304 (Nov. 1991).
Feder et al. (1984) Int. Opthal. 7:87–93.
Epstein et al. (1986) Invest. Ophthalmol. Vis. Sci. 27:387–395.
Kampik et al. (1981) Am. J. Ophthalmol. 91:573–587.
Shiuey et al. (1992) Abstract 2332-7 Invest. Ophthalmol. Vis.
Alvarado et al. (1986) Arch. Ophthal. 104:1517–1528.
Murphy et al. (1992) Arch. Ophthal. 110:1769–1778.
Acott et al. (1989) Am. J. Ophthalmol. 107:1–6.
Dueker et al. (1990) Invest. Ophthalmol. Vis. Sci. 31:115–124.
Alvarado et al. (1992) Arch. Ophthalmol. 110:1779–1785.
Shiuey et al. (1993) Abstract 3365-11 Invest. Ophthal. Vis.
Alvarado et al. (1984) Ophthal. 91:564–579.

Primary Examiner—Michael G. Wityshyn
Assistant Examiner—Jean C. Witz
Attorney, Agent, or Firm—Townsend and Townsend and Crew LLP

[57] ABSTRACT

The treatment of glaucoma and other conditions relating to diseased trabecular meshwork in the eye is effected by administration of macrophages and/or cytokines to the eye. Increased levels of macrophages within the anterior chamber of the eye will at least partially clear obstruction of the trabecular meshwork and restore viability of trabecular cells in order to enhance release of aqueous fluid from the anterior chamber and reduce intraocular pressures. The administration of cytolines will either recruit macrophages or will effect repair of the trabecular meshwork cells directly.

6 Claims, 10 Drawing Sheets

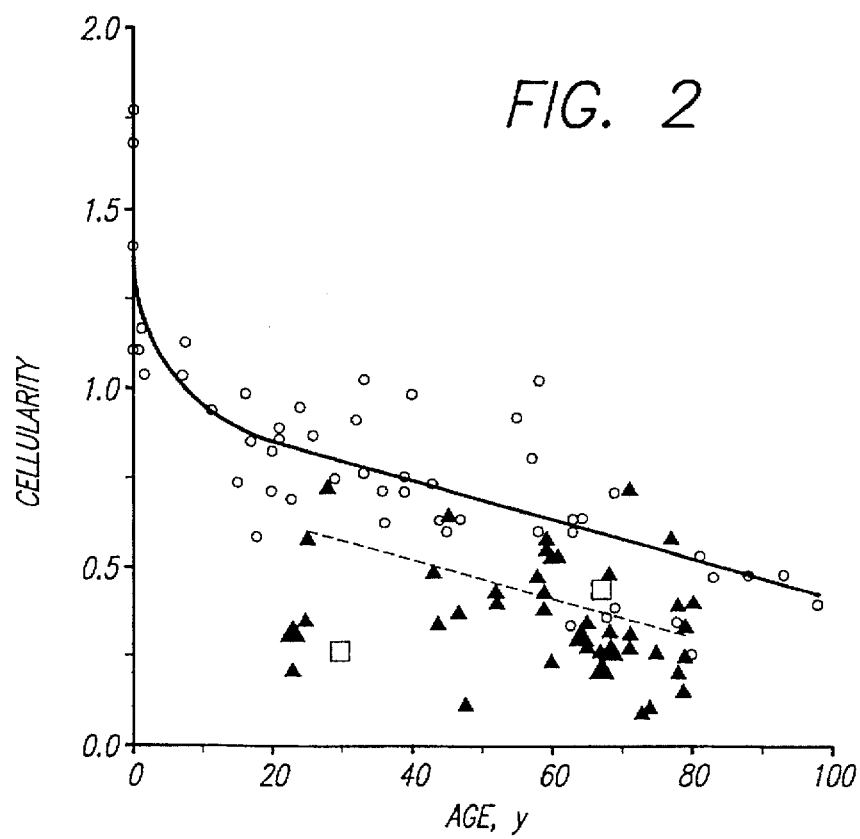
FIG. 2
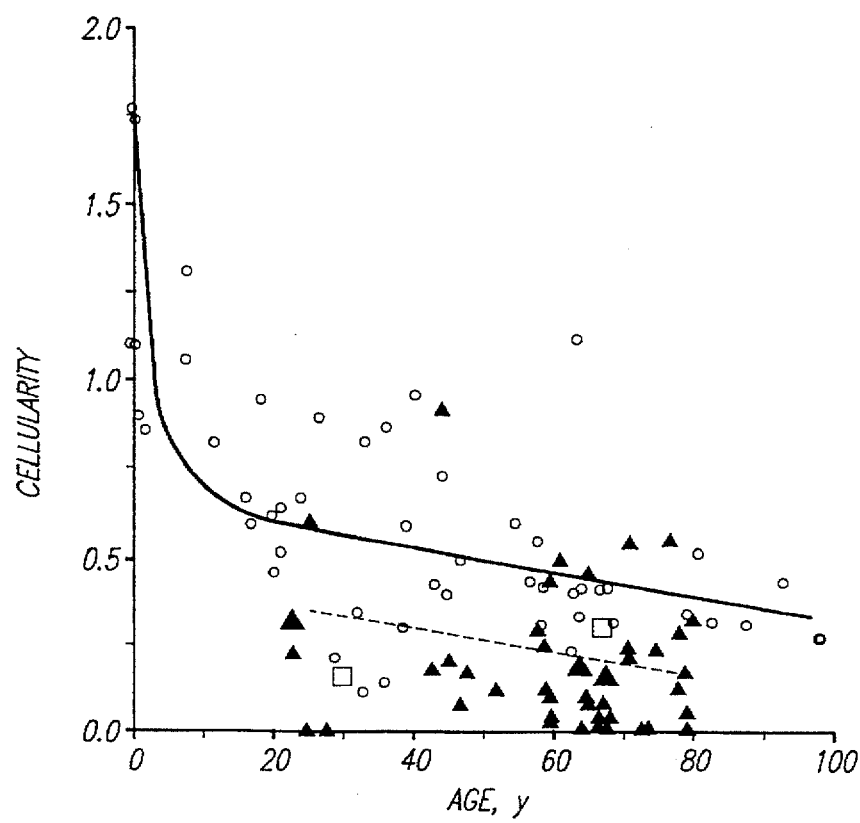

OCULAR THERAPY WITH HOMOLOGOUS MACROPHAGES

BACKGROUND OF THE INVENTION

This invention was supported in part by grants EY 02068 and EY 08835 from the National Eye Institute, National Institutes of Health. The government may have certain rights to this invention.

FIELD OF THE INVENTION

The present invention relates generally to methods and compositions for lowering intraocular pressure and more particularly to the administration of macrophages and/or cytokines to the eye to lower intraocular pressure for treatment of glaucoma and other conditions.

Glaucoma is an ocular disorder that is often manifested as an elevated intraocular pressure (pressure inside the eye). The intraocular pressure rises because the eye fluid or aqueous humor encounters an increased resistance upon leaving a glaucomatous eye. Aqueous humor usually reaches the front part of the eye or anterior chamber through the pupil. It then passes through a circular drainage system known as the trabecular meshwork and returns to the circulation through a vein known as Schlemm's canal. In patients with glaucoma, the trabecular meshwork presents an abnormally high resistance to the passage of aqueous fluid. The resulting pressure elevation is deleterious because it can damage the optic nerve, causing loss of the field of vision, and even blindness, if left untreated.

Current treatment modalities to lower intraocular pressure include the application of microscopic Argon laser burns to the trabecular meshwork (laser trabeculoplasty or LTP), use of topical and systemic medications, as well as glaucoma filtration and other surgery. None of these therapeutic approaches is directed toward repair of the basic cellular abnormality in glaucoma, which is progressive, and which usually becomes increasingly difficult to control.

The abnormality of the trabecular meshwork in pigmentary glaucoma (PG) and in primary open-angle glaucoma (POAG), is not fully understood. For PG, it has been believed that the problem is related to a buildup of pigment in the very thin and externalmost portion of the trabecular meshwork known as the juxtacanalicular tissue (JXT).

It would therefore be desirable to identify with greater particularity the pathogenesis of PG, POAG, and other glaucomatous conditions. Based on such knowledge, it would be further desirable to provide methods and compositions for treating these conditions, where the methods and compositions should be effective with few or no side effects, be safe and not toxic, and be applicable to a variety of conditions, particularly PG and POAG, and preferably be biologically based to mimic the natural debridement mechanisms of the eye.

DESCRIPTION OF THE BACKGROUND ART

Feder and Dueker (1984) Int. Ophthalmol. 7:87–93, describes the injection of peritoneal macrophages into the eyes of experimental rabbits to determine if the macrophages would obstruct aqueous outflow. No pressure elevation in the eyes was detected. Epstein et al. (1986) Invest. Ophthalmol. Vis. Sci. 27:387–395, describes a pigmentary dispersion model for glaucoma in monkeys, where pigment was infused directly into the anterior eye of each test animal. One week after infusion, pigment-laden macrophages were observed in the aqueous channels. Kampik et al. (1981) Am. J. Ophthalmol. 91:573–587 describes the detection of macrophages and dispersed pigment in the trabecular meshwork of patients suffering from pigment dispersion syndrome associated with increased intraocular pressure. Shiuey et al. (1992) Invest. Ophthalmol. Vis. Sci. 33:Abstract 2332-7 reported that laser injury resulted in inductions and later suppressions of mRNA for gene transcription, cell recruitment, and other factors in cultured human trabecular meshwork cells. Alvarado et al. (1986) Arch. Ophthal. 104:1517–1528, failed to find abnormality in the JXT which could account for POAG. Alvarado et al. (1984) Ophthal. 91:564–579 described cell loss in the uveoscleral and corneoscleral meshwork components of the trabecular meshwork in POAG. Murphy et al. (1992) Arch. Ophthalmol. 110:1769–1778, reports a similar pattern of cell loss in PG. Acott et al (1989) Am. J. Ophthalmol. 107:1–6 found that laser trabeculoplasty stimulated cell division in organ-cultured human trabecular meshwork tissue, and Dueker et al (1990) Invest. Ophthalmol. Vis. Sci. 31:115–24 reported a similar stimulation following laser trabeculoplasty in monkey eyes.

Portions of the experimental work in the present application were first reported in Alvarado and Murphy (1992) Arch. Ophthalmol. 110:1779–1785. Shiuey et al. (1993) Invest. Ophthalmol. Vis. Sci. 34: Abstract 3365–11, reported that Argon laser treatment results in synthesis and release of IL-1α by trabecular meshwork cells grown in culture.

SUMMARY OF THE INVENTION

The present invention is based in part on the discovery that restoration of depleted trabecular cells and debridement and clearance of particulate matter from the trabecular meshwork are mediated by host macrophages. In particular, it has been discovered that aqueous channels within the sponge-like trabecular meshwork define finger-like structures. The cumulative area of these structures can be computed using methods described in the Experimental section hereinafter. Each such specialized finger-like structure contains a lining formed by trabecular cells which allows fluid to pass through it with a certain resistance. As a consequence of trabecular cell loss, the walls of these channels can stick together so that they collapse and ultimately disappear. Since the loss of area of these channels could be determined precisely, and since the resistance offered to the fluid passage by the cellular lining of each terminus or finger-like structure can thus be estimated, the increase in resistance resulting from these alterations has been calculated, confirming that the extent of channel loss is sufficient to account for the increase in resistance known to exist in the glaucomatous drainage system. Therefore, development of glaucoma in PG and POAG appears to be related to reduction of outflow channels following the loss of trabecular cells lining these structures. Thus, trabecular cells have an important role in the regulation of aqueous outflow normally as well as in development of glaucoma.

The present invention provides a method for restoring and clearing the trabecular meshwork in patients suffering from a damaged trabecular meshwork, as found particularly in glaucomatous conditions such as PG and POAG, wherein the method comprises introducing or eliciting macrophages in the anterior chamber of an affected eye, preferably by directly introducing macrophages and/or by administering a cytokine to the anterior chamber into an amount effective to recruit macrophages into the chamber. The macrophages are preferably autologous (i.e., obtained from the treated host), and may be produced by harvesting patient or other monocytes, usually from peripheral blood, and growing out the monocytes in vitro to produce macrophages. Such methods are particularly useful for the clearance of particulate matter which can block the trabecular framework to cause a potentially deleterious increase in intraocular pressure. Alternatively, cytokines introduced to the eye may act directly to restore cells of the trabecular meshwork.

In another aspect of the present invention, other macrophages-treatable conditions may be treated by autologous macrophages transplantation where monocytes are harvested, typically from peripheral blood, and grown out in vitro to produce the macrophages to be transplanted. These methods are particularly useful for autologous transplantation where the monocytes are obtained from the peripheral blood of the host to be treated. Exemplary ocular conditions to be treated include degenerative and inflammatory ocular conditions affecting the retina, such as age-related macular degeneration, and other ocular tissues, such as uveitis or malignancies.

In yet another aspect of the present invention, a ophthalmic compositions comprise macrophages present in ophthalmically acceptable carrier in an amount effective to restore trabecular meshwork cells when administered to an eye having an impaired trabecular framework. Alternatively, ophthalmic compositions may comprise a cytokine present in an ophthalmically acceptable carrier in an amount effective to recruit macrophages and/or directly effect a reparative response when administered to the anterior chamber of an eye having an impaired trabecular framework.

BRIEF DESCRIPTION OF THE FIGURES

FIG. 2. Cellularity in two regions of the trabecular meshwork for four diagnosis categories. The data of 55 nonglaucomatous normal eyes (NL) (circles) and 39 eyes from patients with primary open-angle glaucoma (small triangles) and the calculated regression lines are obtained from reference 10 (see end of Experimental section) In both the corneoscleral (left) and uveoscleral (right) meshworks, cellularity for six eyes with pigmentary glaucoma (large triangles) and two with pigment dispersion syndrome (squares) appears depressed compared with that of NL. No such differences were seen for the juxtacanalicular tissue (not shown).

DESCRIPTION OF SPECIFIC EMBODIMENTS

Figure 1:
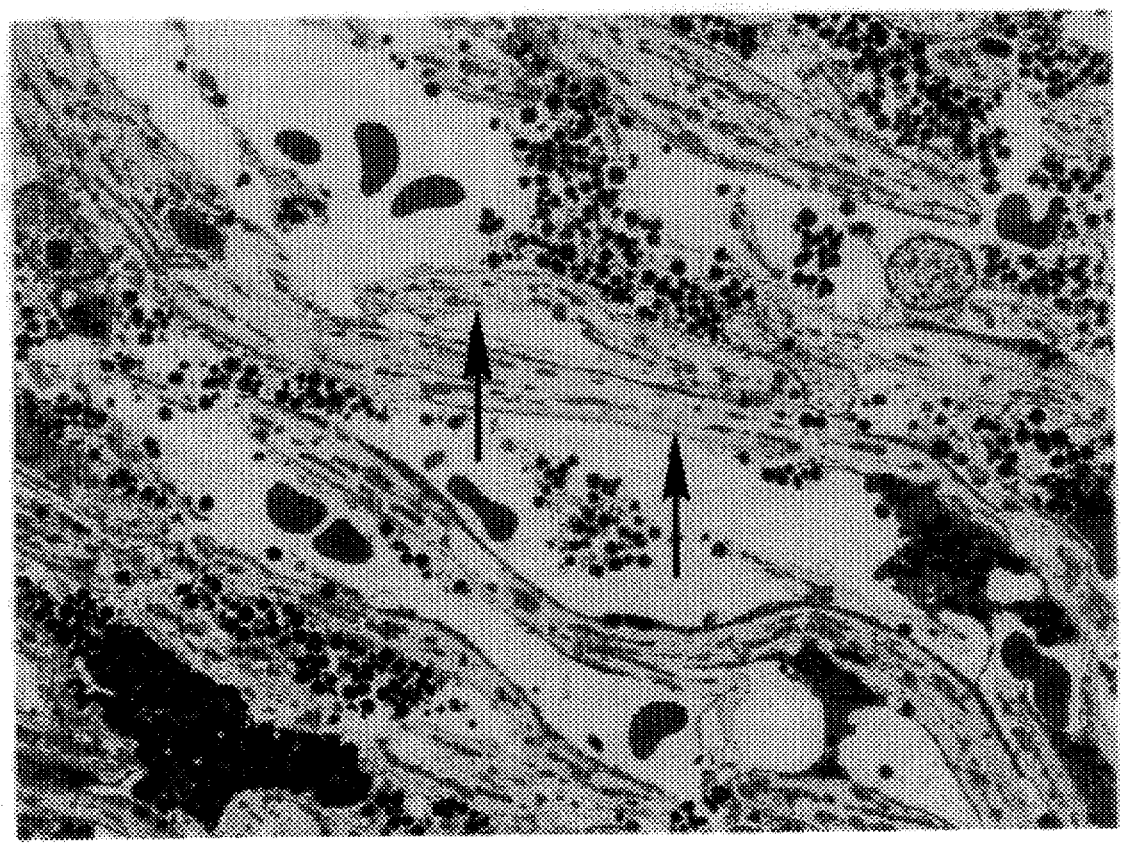
FIG. 1. Transmission electron micrograph of corneoscleral meshwork in pigmentary glaucoma. Note denudation (absence of cellular covering) of trabecular sheets (arrows), pale cytoplasm and fragmented cell membranes of trabecular cells, and necrotic nuclei without cytoplasm. Most melanin granules are intracellular, contained within intact or partially ruptured trabecular cells (specimen 1362; uranyl acetate-lead citrate, x1800).

The methods and compositions of the present invention are intended for treatment for glaucoma and other conditions which manifest elevated intraocular pressure in the eye of a patient, particularly human patients, but also including other mammalian hosts. Glaucoma is a term which embraces a group of ocular diseases characterized by elevated intraocular pressure levels which can damage the eye. Elevated intraocular pressures are generally considered to be those which exceed 20 mmHg, and it is desirable that such elevated pressures be lowered to below about 18 mmHg. Glaucomas are well-described in the medical literature. See, e.g., Leibowitz et al. (1980) Surv. Ophthalmol. 24 (Suppl.): 366–400 and Leske (1983) Am. J. Epidemiol. 118:166–191. Of particular interest to the present invention are glaucomas and other conditions caused by dysfunction of the trabecular meshwork in the anterior chamber of the eye, where the dysfunction can result from either blockage of the fluid-conducting intertrabecular spaces or aqueous channels which occur throughout the corneoscleral meshwork, or from trabecular cell death leading to outflow obstruction by reduction of the area of the aqueous channels. In particular, these conditions include primary open-angle glaucoma (POAG) which results from outflow obstruction secondary to loss of the trabecular cells, and pigmentary glaucoma (PG) which results from cell loss as well as from obstruction of the intertrabecular spaces with matter such as pigment.

In addition to treatment of such glaucomatous conditions, the present invention provides methods for macrophages reintroduction (or autotransplantation) to a host suffering from a macrophages-treatable condition (ocular as well as non-ocular). Such conditions include, but are not limited to, glaucomatous conditions as described above, and comprise introduction of macrophages to a location in the host's body which manifests the condition, i.e., the anterior chamber of the eye in the case of glaucoma treatment, or a joint in the case of joint disease. The macrophages will preferably be autologous, i.e., being obtained from the host to be treated, but may be heterologous if steps to avoid rejection (graft vs. host disease) are taken. Other macrophages-treatable conditions include degenerative disorders such as age-related macular degeneration affecting the retina and some inherited dystrophies affecting the retina, inflammatory conditions such as uveitis affecting other ocular tissues, sarcoidosis, lens-induced uveitis, glaucomato-cyclitic crisis and certain malignancies (e.g., reticulin-cell sarcoma, other ocular tumors). Non-ocular tissues may include degenerative joint diseases (i.e., rheumatoid arthritis).

As described in detail in the Experimental Section hereinafter, it has been observed by the inventors herein that macrophages are involved in a host's natural response to glaucoma. In PG, for example, macrophages are recruited to the trabecular meshwork, which includes the intertrabecular spaces which provide for the free passage of aqueous humor from the eye and which, when blocked, will cause the elevated intraocular pressure which is symptomatic of glaucoma. The macrophages also appear to mediate repair of damaged meshwork tissues by promoting cell division to restore a depleted trabecular cell population and/or rebuilding of the extracellular matrix of the trabecular meshwork tissues. In POAG, the macrophages will be involved in the restoration of trabecular cells to their normal numbers.

In a preferred method according to the present invention, macrophages activated in in vitro cell culture will be administered directly into the anterior chamber of the eye by injection. The macrophages will preferably be homologous, i.e., obtained from the same species as the host being treated, usually being human for the treatment of human patients, and will more preferably be autologous, i.e., obtained directly from the host to be treated. The macrophages will initially be isolated as immature monocytes from the patient or other donor, conveniently by harvesting from peripheral blood.

A protocol for monocyte isolation and activation is as follows:

Blood (20 ml) is drawn from the anti-cubital vein of the patient to be treated (or other donor) and collected in heparinized tubes for isolation of monocytes. Blood (20 ml) is also placed in non-heparinized tubes to obtain autologous serum. Human monocytes are isolated by Percoll density gradient centrifugation (as described by Haraguchi et al. (1992) Cellular Immunol 141:388 and Ulmer and Flad (1979) J. Immunol. Methods 30:1). Briefly, 10 ml of blood is layered onto a discontinuous gradient consisting of 1.08, 1.07 , and 1.064 g/ml Percoll. The gradient is spun in a Beckman model TJ-6 centrifuge at 390 g for 30 min at room temperature. The monocyte fraction is removed (density gradient fraction <1.064 g/ml), rinsed with phosphate-buffered saline, pH 7.4, and resuspended in RPMI 1640 media containing 20% autologous serum. The serum is added to prevent the cells from adhering to each other and to containers. This method usually results in the isolation of $1 \times 10^6$ monocytes/ml of blood.

Activation of monocytes is accomplished by the addition of bacterial lipopolysaccharide to the culture (final concentration=100 ng/ml) or by other suitable methods such as low oxygen treatment (Knighton and Banda, (1983) Science 221:1283–5).

Reintroduction of the activated macrophages into the anterior chamber is done with a 30 gauge needle. 0.1 ml of aqueous is withdrawn and replaced with 0.1 ml of suspended macrophages. Suitable concentrations will generally be in the range of $4 \times 10^5$ to $1 \times 10^7$ cells/ml.

In an alternative embodiment of the present invention, macrophages may be recruited in situ within the eye by administering an amount of a cytokine effective to attract endogenous macrophages to the anterior chamber and trabecular framework. Cytokines isolated from the cultured macrophages could also be administered directly to promote trabecular cell division or other repair of trabecular tissues, or to induce trabecular or Schlemm's canal endothelial cells to produce secondary cytokines. Preferred cytokines include IL-1α, , CSF-1, and TNF-α, with IL-1α being presently most preferred.

The cytokines may be administered directly to the anterior chamber of the eye, e.g., by injection, or may be administered indirectly, e.g., by topical application to the eye, with the amounts of cytokine being sufficient to recruit macrophages at a level effective to treat and repair the injured trabecular meshwork or to restore cells of the trabecular meshwork directly.

Thus, compositions according to the present invention will be suitable for direct administration to a patient's eye. By "direct administration" it is meant that the compositions will be applied topically or by injection or installation, into the eye so that they will be transported where the compositions will be therapeutically effective.

By "therapeutically effective" it is meant that the compositions will result in clearance and/or restoration of the trabecular cells of the trabecular meshwork. In the case of glaucoma treatment, it is meant that the compositions will be present in amounts effective to lower the intraocular pressure of the eye, particularly when the intraocular pressure was previously elevated, i.e., above about 20 mmHg.

The effective treatment agents of the present invention, i.e., macrophages and/or cytokines, will be incorporated into suitable ophthalmically acceptable carriers at concentrations chosen to be effective when administered to the eye. In the case of macrophages compositions, macrophages will usually be present in concentrations from about $4 \times 10^5$ cells/ml to $10^7$ cells/ml. Such compositions will be suitable for administered dosages of about 0.1 ml, resulting in a total delivery of macrophages in the range from about $4 \times 10^4$ to $10^6$ cells.

Compositions according to the present invention incorporating cytokines will usually have a concentration in the range from about 0.1 weight percent to 10 weight percent, more usually from about 0.5 weight percent to 1 weight percent, with the particular concentration depending on which cytokine is being employed. It will also be possible to incorporate the cytokines into controlled-release formulations and articles, where the total amount of cytokine is released over time, e.g., over a number of minutes or hours. Typically, the total dosage of the cytokine will be within the limits described above for non-controlled-release formulations, but some cases may be greater, particularly when the controlled-release formulations act over relatively long periods of time. Suitable controlled-release articles for use with the compositions of the present invention include solid ocular inserts available from commercial vendors such as Alza Corporation, Palo Alto, Calif., and from Oculex Corporation, Palo Alto, Calif.

Topical compositions for delivering cytokines according to the present invention will typically comprise the cytokine present in a suitable ophthalmically acceptable carrier, including both organic and inorganic carriers. The exemplary ophthalmically acceptable carriers include water, buffered aqueous solutions, isotonic mixtures of water and water-immiscible solvents, such as alkanols, aryl alkanols, vegetable oils, polyalkalene glycols, petroleum-based jellies, ethylcellulose, ethyloleate, carboxymethylcelluloses, polyvinylpyrrolidones, isopropyl myristates, and the like. Suitable buffers include sodium chloride, sodium phosphate, sodium borate, sodium acetate, sodium gluconate, and the like. Formulations of the present invention may also contain ophthalmically acceptable auxiliary components, such as emulsifiers, preservatives, wetting agents, thixotropic agents, e.g., polyethylene glycols, antimicrobials, chelating agents, and the like. Particularly suitable antimicrobial agents include quarternary ammonium compounds, benzalkonium chloride, phenylmercuric salts, thimerosal, methyl paraben, propyl paraben, benzyl alcohol, phenylethanol, sorbitan, monolaurate, triethanolamine oleate, polyoxyethylene sorbitan monopalmitylate, dioctyl sodium sulfosuccinate, monothioglycerol, and the like. Ethylenediamine tetracetic acid (EDTA) is a suitable chelating agent.

The following examples are offered by way of illustration, not by way of limitation.

EXPERIMENTAL

Materials and Methods

Two series of specimens were examined for this study. A description of the first series consisting of 27 patients and 33 specimens is given in Table 1.

TABLE 1

Clinical Findings and Specimen Characteristics*

| Diagnostic Group | Patient Age/Sex | Medications † | Specimen No. | Intraocular Pressure, mm Hg | Specimen Source |
|---|---|---|---|---|---|
| PG | 23/M | Epinephrine hydrochloride, timolol maleate, pilocarpine hydrochloride, acetazolamide | 0169 | 30 | T |
|  |  |  | 0186 | 30 | T |
|  | 64/F | Pilocarpine, timolol, acetazolamide | 0834 | 44 | T |
|  | 67/M | Epinephrine, timolol, pilocarpine, acetazolamide | 1243 | 33 | T |
|  |  |  | 1314 | 30 | T |
|  | 68/M | Epinephrine, pilocarpine, acetazolamide, betaxolol hydrochloride | 1362 | 37 | T |
| PDS | 30/F | . . . | 0619 | 13 | Eyes |
|  | 67/M | Epinephrine, timolol | 0845 | 18.8 (±3.3) | Eyes |
| POAG | 60/M | Acetazolamide, carbachol | 0846 | 56 | T |
|  |  |  | 0892 | 51 | T |
|  | 62/F | Pilocarpine | 0977 | 26 | Eyes |
|  | 62/M | Pilocarpine, acetazolamide, betaxolol, methazolamide | 1335 | 27 | T |
|  | 63/F | Timolol, pilocarpine | 0691 | 25 | T |
|  | 65/M | Epinephrine, timolol, pilocarpine, acetazolamide, echothiophate iodide | 0263 | 45 | T |
|  | 65/F | Epinephrine, acetazolamide, carbachol | 0032 | 32 | T |
|  | 65/M | Epinephrine, timolol, pilocarpine, acetazolamide | 0374 | 33 | T |
|  | 67/M | Pilocarpine, acetazolamide | 0613 OU | 31/26 | Eyes |
|  | 67/M | Timolol, pilocarpine, betaxolol | 1344 | 40 | T |
|  | 68/F | Epinephrine, pilocarpine, acetazolamide | 0303 | 24 | T |
|  | 68/F | Epinephrine, timolol, pilocarpine | 0373 | 24 | T |
|  | 71/F | Acetazolamide, carbachol | 0515 Ou | . . . | Eyes |
|  | 71/M | epinephrine, pilocarpine, acetazolamide, echothiophate | 0612 OU | 32 | Eyes |
| NL eyes | 63/F | . . . | 0274 | . . . | Eyes |
|  | 63/M | . . . | 0433 | . . . | Eyes |
|  | 64/ . . . | . . . | 0336 | . . . | Eyes |
|  | 64/M | . . . | 0406 | . . . | Eyes |
|  | 63/F | . . . | 0708 | . . . | Eyes |
|  | 68/F | . . . | 0410 | . . . | Eyes |
|  | 69/M | . . . | 0127 | . . . | Eyes |
|  | 69/M | . . . | 0199 | . . . | Eyes |

TABLE 1-continued

Clinical Findings and Specimen Characteristics*

| Diagnostic Group | Patient Age/Sex | Medications † | Specimen No. | Intraocular Pressure, mm Hg | Specimen Source |
|---|---|---|---|---|---|

*Intraocular pressure indicates highest recorded; PG, pigmentary glaucoma; T, trabeculectomy; PDS, pigment dispersion syndrome; POAG, primary open-angle glaucoma; and NL, normal nonglaucomatous. For specimen 0845, intraocular pressures measured during a 19-year period were averaged. This patient had a facility of outflow of 0.24, and no visual field defects or disc changes were observed during this time.
† Medications include all of those used during the course of treatments.

This series consisted of four patients with PG (six specimens), two with pigment dispersion syndrome (PDS) (two specimens), 13 with POAG (17 specimens), and eight with nonglaucomatous normal eyes (NL) (eight specimens). The POAG and NL specimens were selected from patients in the seventh decade of life to match the older age of PG and PDS specimen donors. The second series consisted of 26 additional NL specimens used to measure the extent to which the cul-de-sacs were lined by trabecular cells. The PG and PDS specimens are described in Murphy et al. (1992)[1], and all of the remaining POAG and NL specimens had been described in our previous reports[3,9–11] except for specimens 1335 and 1344. Whenever specimens from both eyes were examined, we used the means of the measurements obtained for our calculations.

Specimens obtained after surgical procedures such as trabeculectomy or enucleation were immersion fixed within 30 seconds of excision. Others were obtained and fixed by immersion a few hours after death when the eyes were enucleated, as detailed elsewhere.[1,3,9–11] Light micrographs (X 1700) of the TM and transmission electron micrographs (X 2600 and X 6500) of the JXT and adjacent tissues were assembled into montages as described previously.[1,3,9–11]

Morphometry was done with a SigmaScan program (Jandel Scientific, Corte Madera, Calif.) on a Summagraphics digitizing pad (Fairfield, Conn.) interfaced with an IBM PC XT. The digitizer was calibrated daily. The photographic montages were overlaid with a transparent plastic sheet, and the structures of interest were marked with ink to leave a permanent record and traced with a cursor to measure their lengths or areas. Investigators performing the measurements were masked regarding the diagnosis and age of the patients. Four structural features and the identity of a specific group of cells in the TM were evaluated as follows.

Cell Density or Cellularity

The cell density was measured by counting the trabecular cell nuclei present in a given tissue area (excluding aqueous channels) on light micrographs (X 1700). The ratio of the number of nuclei per tissue area is a quantity referred to as cellularity. Cellularity was calculated for the entire TM and three subregions, as described in a previous report,[10] including a portion of the corneoscleral meshwork, the uveoscleral meshwork, and the JXT, in the four specimens from patients with PG and in the two from patients with PDS. We then compared these data with standards for NL and POAG specimens, which we had previously published.[10]

Representation of Aqueous Channels

To determine the proportionate area of aqueous channels in a defined tissue region, we used light micrographs (X 1700) to sample a 160-μm² rectangular area (i.e., the "intermediate" zone of previous reports[10]) located in the midregion of the corneoscleral meshwork. For this survey, as outlined in Table 2, we used specimens from 24 patients, including four with PG, two with PDS, 11 with POAG, and seven with NL. The patients with POAG and NL were age matched and compared only with the older group of three patients with PG.

TABLE 2

Fraction of Corneoscieral Meshwork Occupied by Aqueous Channels*

| Diagnostic Group, Specimen No. | Age, y | Aqueous Channel Fraction |
|---|---|---|
| PG | | |
| 0169/0186 | 23 | 0.18 |
| PG (older group) | | |
| 0834 | 64 | 0.18† |
| 1243/1314 | 67 | 0.21† |
| 1362 | 68 | 0.13 |
| Mean ± SD | 66.3 ± 2.1 | 0.17 ± 0.04 |
| POAG | | |
| 0846 | 60 | 0.10 |
| 0977 | 62 | 0.24 |
| 0691 | 63 | 0.12 |
| 0032 | 65 | 0.29 |
| 0263 | 65 | 0.27 |
| 0374 | 65 | 0.21 |
| 0613 | 67 | 0.11† |
| 0303 | 68 | 0.25 |
| 0373 | 68 | 0.10 |
| 0515 | 71 | 0.15† |
| 0612 | 71 | 0.15† |
| Mean ± SD | 65.9 ± 3.5 | 0.18 ± 0.07 |
| PDS | | |
| 0619 | 30 | 0.38 |
| 0845 | 67 | 0.33 |
| NL | | |
| 0274 | 63 | 0.34 |
| 0708 | 63 | 0.35 |
| 0336 | 64 | 0.25 |
| 0406 | 64 | 0.19 |
| 0410 | 68 | 0.38 |
| 0127 | 69 | 0.26 |
| 0199 | 69 | 0.22 |
| Mean ± SD | 65.7 ± 2.8 | 0.28 ± 0.07 |

*PG indicates pigmentary glaucoma; POAG, primary open-angle glaucoma; PDS, pigment dispersion syndrome; and NL, normal, nonglaucomatous eyes. Values are fraction of a standard 160-μm² rectangle of the corneoscleral meshwork. The POAG and NL specimens are age matched to specimens from the older patients with PG.
†Mean of specimens from two eyes, same patient.

Surface Area of Cul-de-sacs

Figure 1A:
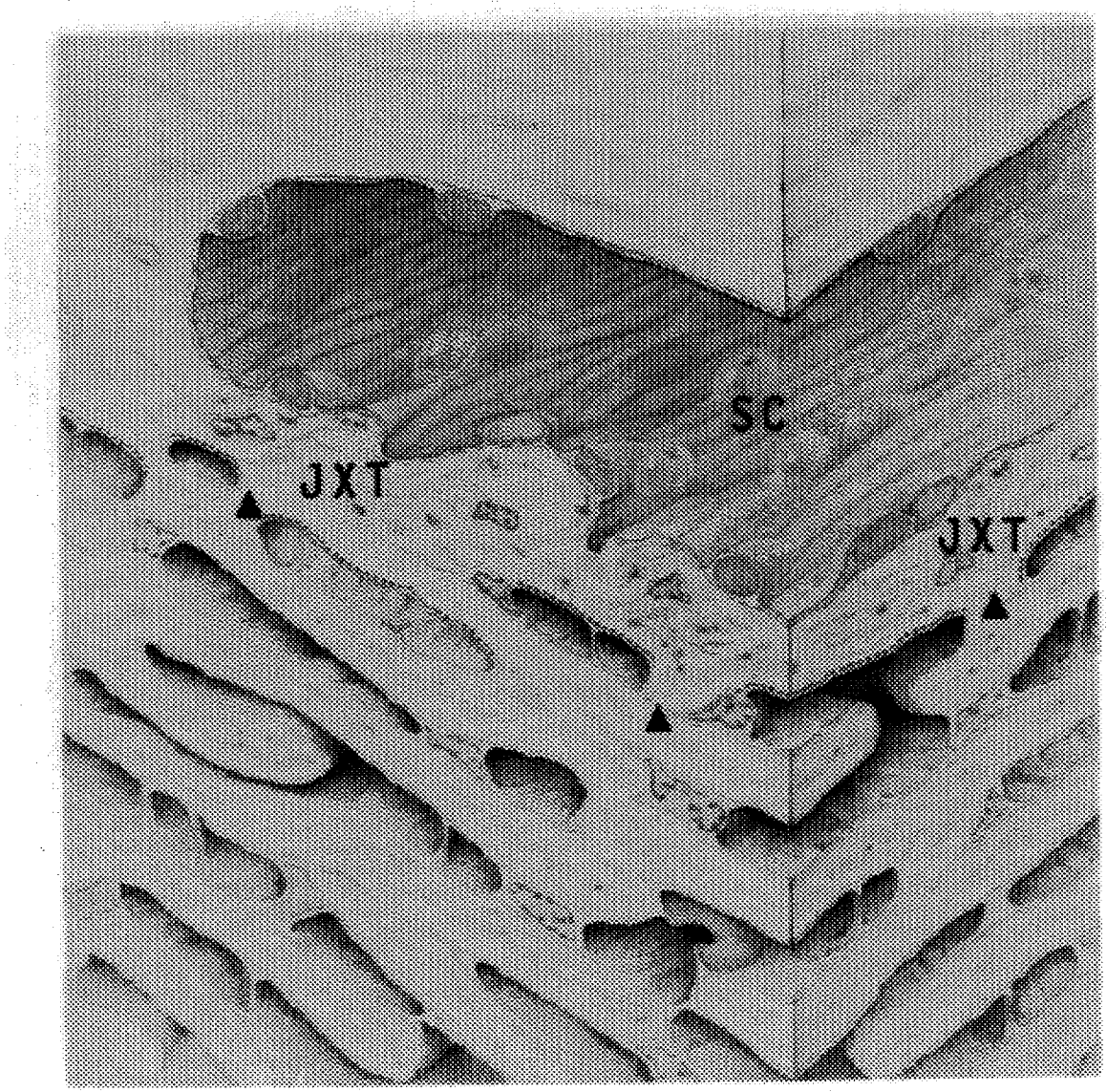
FIG. 1A. The inner juxtacanalicular tissue (JXT) is shown in relation to Schlemm's canal (SC). The JXT contains collagen (light pink), plaque material (gray), cells (magenta), and regions that are electron-lucent in transmission electron micrographs (aqua). The outer side of the JXT is covered by a monolayer of endothelial cells (yellow), which line SC. On its inner aspect, the JXT merges with the extracellular matrix of the corneoscleral meshwork in some places (arrowheads); in other places, the JXT is bound by the terminations of the outermost aqueous channels (purple) of the corneoscleral meshwork. Before reaching the JXT, the aqueous humor must traverse these trabecular cell-lined channels, which are referred to as the "cul-de-sacs" (broken lines). We measured the aggregate length of the cul-de-sacs as they abut against the JXT to obtain an assessment of their representation.

Referring to FIG. 1A, the outermost terminations of aqueous channels that abut the internal boundary of the JXT as cul-de-sacs. These cul-de-sacs are regularly disposed within 5 to 10 μm of the inner wall of Schlemm's canal (SC), which makes their identification straightforward. We measured the aggregate length of cul-de-sacs (ΣS) in relationship to the length of the associated inner wall of SC (L) n meridional sections. The following assumptions were made to estimate the area occupied by cul-de-sacs. (1) The cul-de-sacs are randomly distributed along the inner wall of SC and are equally numerous when sampled in any orientation. (To test whether the orientation of sections alters the cul-de-sac measurements, we compared numbers and lengths of cul-de-sacs in sections taken meridionally and along the long axis of the canal at 90° to the meridional plane in the same specimen [No. 0433]. The average length of cul-de-sacs [14.1 vs 14.8 μm] and their number per length of the inner wall of SC [1 per 30 μm vs 1 per 36 μm] are virtually the same in either orientation.) (2) The mean length across cul-de-sacs in any orientation is equal to ΣS/n, where n equals the number of cul-de-sacs. (3) If we Consider that these lengths are dimensions of regular geometric areas (i.e., sides of squares or diameters of circles), then we will overestimate or underestimate the true cul-de-sac areas with equal probability. For square areas, the ratio of cul-de-sac area to inner wall area is $(n^2)(\Sigma S/n)^2/L^2$ or $(\Sigma S/L)^2$. For circular areas, the ratio is $(n^2)(\Sigma S/2n)^2 \pi/L^2$ or $(\pi/4)(\Sigma S/L)^2$.

Having determined this relationship, we used published values[19] for the area of the inner wall to compute that of the cul-de-sacs.

As shown in Table 3, data were collected for this age-matched assessment from a subpopulation of 19 patients, including four with PG, two with PDS, seven with POAG, and six with NL, for which electron-microscopic montages (X 2500) of the JXT and neighboring corneoscleral tissues were available.

TABLE 3

Relative Length of Cul-de-sacs*

| Diagnostic Group, Specimen No. | Age, y | Cul-de-sacs, μm | Inner Wall, μm | Ratio of Lengths | Cul-de-sac Area, × 10⁻³ cm² | |
|---|---|---|---|---|---|---|
| | | | | | Squares | Circles |
| PG | | | | | | |
| 0169/0186 | 23 | 118/60 | 304/271 | 0.31† | 11† | 8† |
| PG (older group) | | | | | | |
| 0834 | 64 | 29 | 92 | 0.31 | 11 | 8 |
| 1243/1314 | 67 | 74/103 | 190/170 | 0.39 521 | 17† | 13† |
| 1362 | 68 | 120 | 400 | 0.30 | 10 | 8 |
| Mean ± SD | 66.3 ± 2.1 | ... | ... | 0.33 ± 0.04 | 12 ± 3 | 9 ± 3 |
| POAG | | | | | | |
| 0835/0892 | 60 | 79/49 | 478/210 | 0.20† | 4† | 3† |
| 1335 | 62 | 52 | 247 | 0.21 | 5 | 4 |
| 0977 | 62 | 183 | 316 | 0.58 | 37 | 29 |
| 0691 | 63 | 78 | 268 | 0.29 | 9 | 7 |
| 1344 | 67 | 40 | 169 | 0.24 | 6 | 5 |
| 0515 | 71 | 30 | 95 | 0.32 | 11 | 9 |
| 0612 | 71 | 116 | 373 | 0.31 | 11 | 8 |
| Mean ± SD | 65.7 ± 4.7 | ... | ... | 0.31 ± 0.13 | 13 ± 12 | 10 ± 9 |
| PDS | | | | | | |
| 0619 | 30 | 105 | 181 | 0.58 | 37 | 29 |
| 0845 | 67 | 229 | 381 | 0.60 | 40 | 31 |
| NL | | | | | | |
| 0274 | 63 | 158 | 394 | 0.40 | 18 | 14 |
| 0433 | 63 | 157 | 358 | 0.44 | 21 | 16 |
| 0336 | 64 | 164 | 293 | 0.56 | 34 | 27 |
| 0406 | 64 | 343 | 470 | 0.73 | 59 | 46 |
| 0410 | 68 | 238 | 450 | 0.53 | 31 | 24 |
| 0127 | 69 | 362 | 470 | 0.77 | 65 | 51 |
| Mean ± SD | 65.2 ± 2.6 | ... | ... | 0.57 ± 0.15 | 37 ± 20 | 30 ± 16 |

*PG indicates pigmentary glaucoma; POAG, primary open-angle glaucoma; PDS, pigment dispersion syndrome; and NL, normal, nonglaucomatous eyes. Collective length of cul-de-sac is compared with length of Schlemm's canal inner wall for each specimen. Calculated areas of cul-de-sacs are given for square and circular areas according to formulas given in text.
†Mean of specimens from two eyes, same patient.

Cellular Lining of Cul-de-sacs

The extent of the lining of these structures has not been studied quantitatively. In our 1971 ultrastructural study, we reported that in well-fixed specimens, a complete endothelial lining is generally demonstrable, although it was noted that occasional discontinuities are present.[17] To determine whether the cul-de-sacs have a complete covering or lining of trabecular cells, we measured the cumulative length of the gaps or discontinuities present within the cul-de-sacs on electron micrographs (X 6500) in 32 NL specimens (Table 4). In eight specimens selected at random from this group (Nos. 0543, 0469, 0340, 0745, 0433, 0606, 0626, and 0405), data on size and distribution of these gaps were also obtained.

TABLE 4

Extent of Cellular Coverage of Cul-de-sacs*

| Specimen No. | Age, y | Cellular Coverage |
|---|---|---|
| 0572 | 0.2 | 0.962 |
| 0617 | 0.5 | 0.993 |
| 0565 | 0.9 | 0.950 |
| 0543 | 1.1 | 0.929 |
| 0630 | 7 | 0.981 |
| 0475 | 11 | 0.965 |
| 0409 | 15 | 0.963 |
| 0258 | 17 | 0.993 |
| 0469 | 18 | 0.954 |
| 0340 | 20 | 0.871 |
| 0289 | 21 | 0.956 |
| 0279 | 23 | 0.984 |
| 0391 | 29 | 0.980 |
| 0745 | 33 | 0.986 |
| 1069 | 36 | 0.967 |
| 0257 | 43 | 0.995 |
| 0411 | 47 | 0.965 |
| 0126 | 55 | 0.973 |
| 0783 | 56 | 0.983 |
| 0784 | 58 | 1.000 |
| 0387 | 59 | 0.959 |
| 0433 | 63 | 0.997 |
| 0274 | 63 | 0.988 |
| 0336 | 64 | 0.961 |
| 0496 | 64 | 0.980 |
| 0410 | 68 | 0.975 |
| 0127 | 69 | 0.976 |
| 0267 | 78 | 0.983 |
| 0626 | 80 | 0.989 |
| 0260 | 81 | 0.991 |
| 0593 | 83 | 0.966 |
| 0405 | 93 | 0.979 |
| Mean ± SD | — | 0.972 ± 0.024 |

*Values are calculated as length of segments covered with cells/aggregate length of segments in normal, nonglaucomatous eye specimens from a wide range of patient ages (n = 32).

Identification of Putative Macrophages

At least two types of melanin-containing cells can be observed in PG specimens. One cell type is found lining the trabecular beams and it has many of the attributes of typical TM cells.[16] The other is a large cell type that can be found within the aqueous channels, in the interstitium of the JXT, and in the lumina of SC and the aqueous veins. To identify the second cell type, immunogold assays were used to learn whether the Mac-1 monoclonal antibody (Boehringer Mannheim, Indianapolis, Ind.), which binds to macrophages,[18,19] was also bound by these cells. Tissues were fixed with 2% paraformaldehyde, embedded in LR White (London Resin [a polar monomer polyhydroxylated acromatic acrylic resin], Electron Microscopy Sciences, Fort Washington, Pa.), thin sectioned, and incubated for 1 hour with Mac-1 diluted 1:30, 1:40, and 1:60 in phosphate-buffered saline (PBS). Following several washes in PBS, the tissue was incubated for 1 hour with a secondary antibody (goat anti-mouse IgG bound to 10-nm colloidal gold particles [Janssen, Piscataway, N.J.] diluted 1:40 in PBS). Gold particles were counted on electron micrographs printed at X 25000 and their number per square micrometer of tissue was compared in putative macrophages, trabecular cells, and extracellular regions. Negative controls included tissues treated with PBS instead of primary antibody, and positive controls included a line of cells previously shown to have the Mac-1 antigen.

RESULTS

Cell Density or Cellularity

Figure 2A:
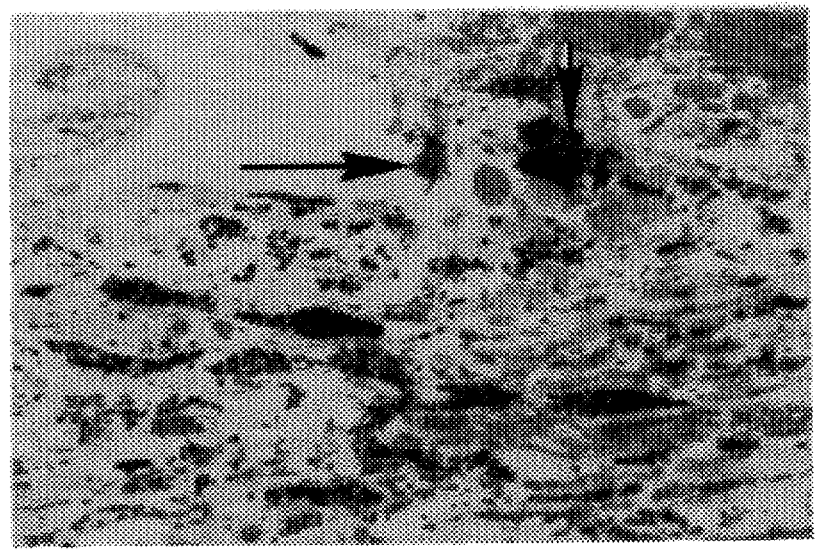
FIGS. 2A and 2B. Removal of pigment from the meshwork by macrophages in pigmentary glaucoma (specimen 1362). Left, Light micrograph of Schlemm's canal. A pigment-filled cell (black arrow) is partially inside the canal lumen and another is close to the lumen (white arrow) (x600). Right, An enormously enlarged, pigment-filled cell is found entirely within the canal lumen (toluidine blue, x600).
Figure 2B:
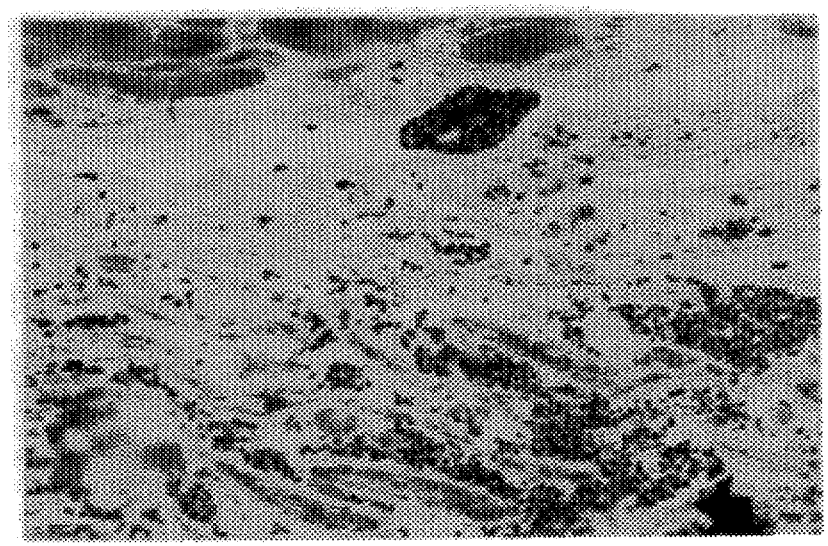

Examination of PG and PDS specimens by electron microscopy shows that many corneoscleral and uveoscleral sheets and cords are devoid of their cellular lining and possess numerous necrotic trabecular cells (FIG. 1). These observations are consistent with those of Richardson et al,[14] who described a similar cell loss in PG. Cell density measurements in the corneoscleral and uveoscleral meshworks in four patients with PG are compared with published standards for patients with POAG[10] in FIG. 2. No formal statistical analysis was performed because of the limited number of PG and PDS specimens. Inspection of this figure shows that cellularities for patients with PG are clustered well below the calculated regression line for patients with POAG, suggesting that the PG specimens have a uniformly depressed cell density. It is also apparent that in the PDS specimens, where by definition a glaucomatous condition is not present, cellularities were also low relative to NL specimens. The JXT differs from the corneoscleral and uveoscleral meshworks in that no cellularity differences were measured among the four diagnostic groups (data not shown). Previously, we had also reported that the cellularity of the JXT in POAG and NL specimens was essentially identical.[10]

Representation of Aqueous Channels

The mean aqueous channel fraction was lower for PG and POAG compared with an age-matched group of NL specimens (Table 2). Although the numbers of specimens are small, these differences are statistically demonstrable (two-tailed t tests, P<0.05). Even in the young patient with PG (specimens 0169 and 0186), the low aqueous channel fraction was lower (0.18) in the corneoscleral meshwork. Of great interest is that the two PDS specimens mentioned earlier to have a decreased cellularity in the corneoscleral meshwork and uveoscleral meshwork seemed to have a normal representation of aqueous channels within the corneoscleral meshwork (Table 2).

Surface Area of Cul-de-sacs

Figure 3:
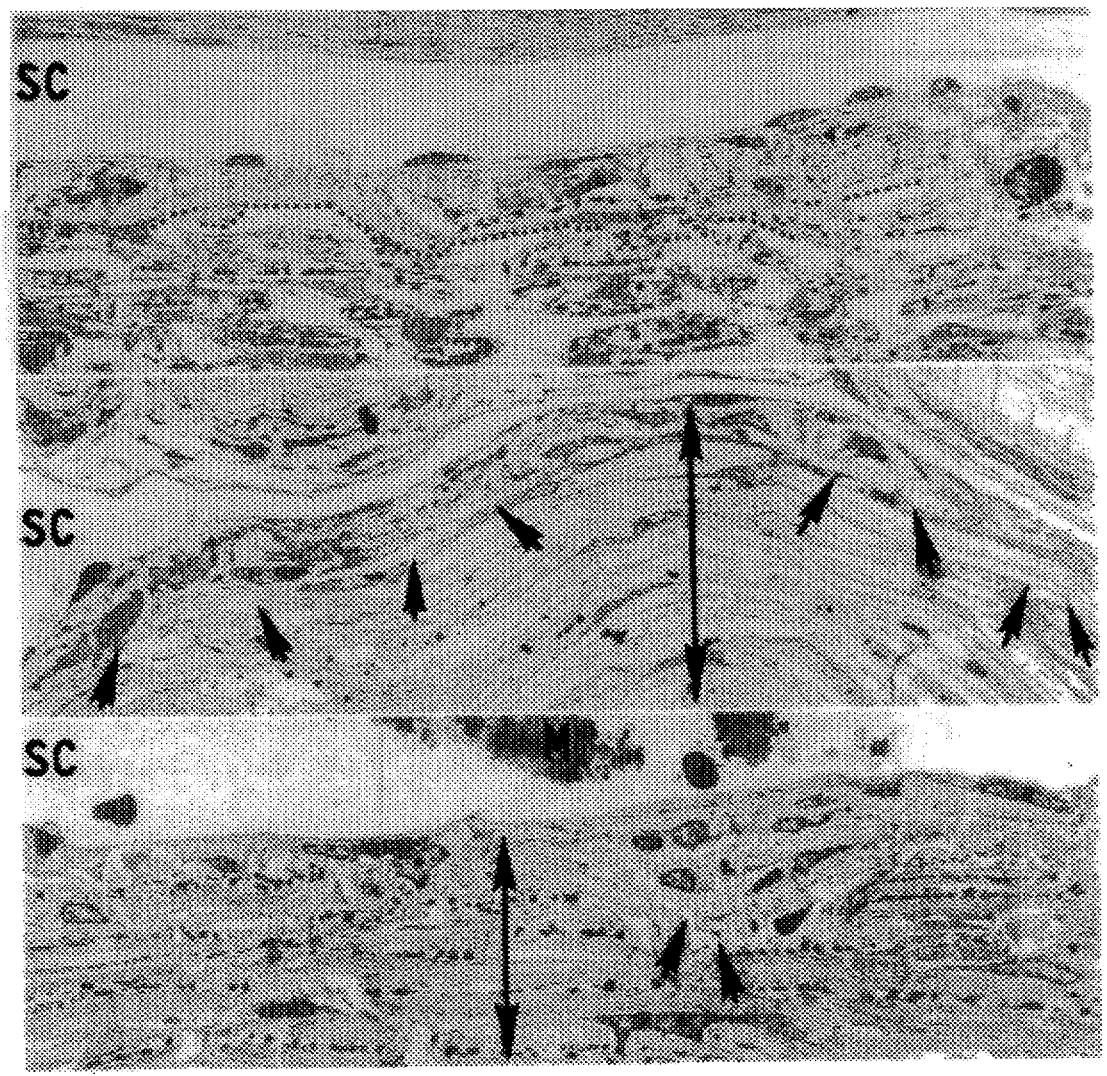
FIG. 3. Comparison of cul-de-sacs in montages of electron micrographs. Schlemm's canal (SC) is toward the top of each montage, and the juxtacanalicular tissue (JXT) is below. Top, Cul-de-sacs abut against JXT at numerous sites in a nonglaucomatous normal eye specimen (broken lines). Note length of the cul-de-sacs compared with length of inner wall of SC (specimen 0433, X 1000). Center, Reduction of cul-de-sacs in a specimen from a patient with pigmentary glaucoma. Fusion of corneoscleral sheets is prominent as indicated by two-headed arrow, where no aqueous channels are observed over a relatively large area. The aggregate length of the cul-de-sacs (distances between short arrows) is equivalent to only 0.43 of the length of the inner wall of SC (specimen 0169, X 1000). Bottom, Specimen from patient with primary open-angle glaucoma with extensive trabecular fusion (two-headed arrow) and obliteration of aqueous channels. Only one small cul-de-sac segment is observed (between arrows). Melanin (M) is in SC (specimen 0846; uranyl acetate-lead citrate, X 1250).

FIG. 3 (top) shows the cul-de-sacs in an NL specimen, where they can be seen to form a major portion of the internal boundary of the JXT. For comparison, we also show the appearance of two markedly affected specimens from patients with PG (FIG. 3, middle) and POAG (FIG. 3, bottom). The aqueous channels are largely collapsed and the cul-de-sacs are few in number. Ratios of cul-de-sacs for all specimens examined are given in Table 3. Examination of this table shows that in patients with NL, the aggregate length of cul-de-sacs is about half the length of the wall of SC. This extent of cul-de-sacs in NL persists irrespective of the length of the inner canal wall (Table 3). In PG and POAG specimens, the ratios are lower than in either NL or PDS specimens. There is a mean reduction of 45% in the linear representation of the cul-de-sacs in the 10 age-matched glaucoma specimens compared with NL. These differences are statistically demonstrable (two-tailed t test for age-matched groups, P<0.05 for PG, P<0.01 for POAG).

As described in the "Materials and Methods" section, we estimated the area of cul-de-sacs from the linear measurements in the following manner. The part of SC that faces flow corresponds to the inner wall area and measures 0.11 $cm^2$.[20] The mean ratio between the length of the cul-de-sacs and the length of the inner wall ($\Sigma S/L$) is equal to 0.57 for NL (Table 3). The mean area of the cul-de-sacs in six NL specimens is equivalent to $(0.57)^2 \times 0.11$ cm$^2$, or 0.036 cm$^2$, using the formula for squares, or equivalent to 0.027 cm$^2$ using the formula for circles (Table 3). The mean area for the 10 age-matched PG and POAG specimens is equivalent to $(0.315)^2 \times 0.11$ cm$^2$ or to 0.011 cm$^2$ using the formula for squares, or equivalent to 0.008 cm$^2$ using the formula for circles. These results show that the difference between POAG and PG compared with NL amounts to a 70% reduction in area. (McEwen[20] assumed that the meridional length of the inner wall is 250 µm and calculated an area of 0.11 cm$^2$. We measured a mean inner wall length of 406 µm obtained for the six NL specimens and 248 µm obtained for the 10 age-matched PG and POAG specimens in this study. Assuming a mean corneal diameter of 12.5 mm at the level of SC, the circumference is 39.3 mm and the area of the inner wall is then 0.16 cm$^2$ for NL and 0.097 cm$^2$ for PG and POAG. The areas of the cul-de-sacs are then estimated using the circle formula to be 0.052 cm$^2$ for NL and 0.0096 cm$^2$ for PG and POAG, or an 82% rather than a 70% reduction.) As with the corneoscleral aqueous channel measurements, the PDS specimens appeared to have the same ratio as the NL specimens, although as already noted, the cellularity was abnormally low.

Cellular Lining of Cul-de sacs

The portion of the cul-de-sacs immediately adjacent to the JXT was lined by trabecular cells along 97% of the linear dimension measured (Table 4). In terms of area, the lining was 94% complete $(0.97)^2$. Thus, only 6% of the area of these channels was not covered by a cellular lining in the NL specimens evaluated. Data obtained from the eight specimens where size and distribution of discontinuities were measured showed a total of 53 small gaps within 111 cul-de-sacs (cellular coverage averaged 96% in these eight specimens). The mean (±SD) length of the gaps was 1.04±0.73 µm and the mean cul-de-sac length was 14.59±4.96 µm. Thus, the 6% area represents the sum of many small, separate discontinuities that are actually sites where the intercellular space is widened. We found no evidence for their clustering, because most of these gaps (39 cases [74%]) occurred as a single discontinuity within a cul-de-sac.

Identification of Putative Macrophages

Figure 4:
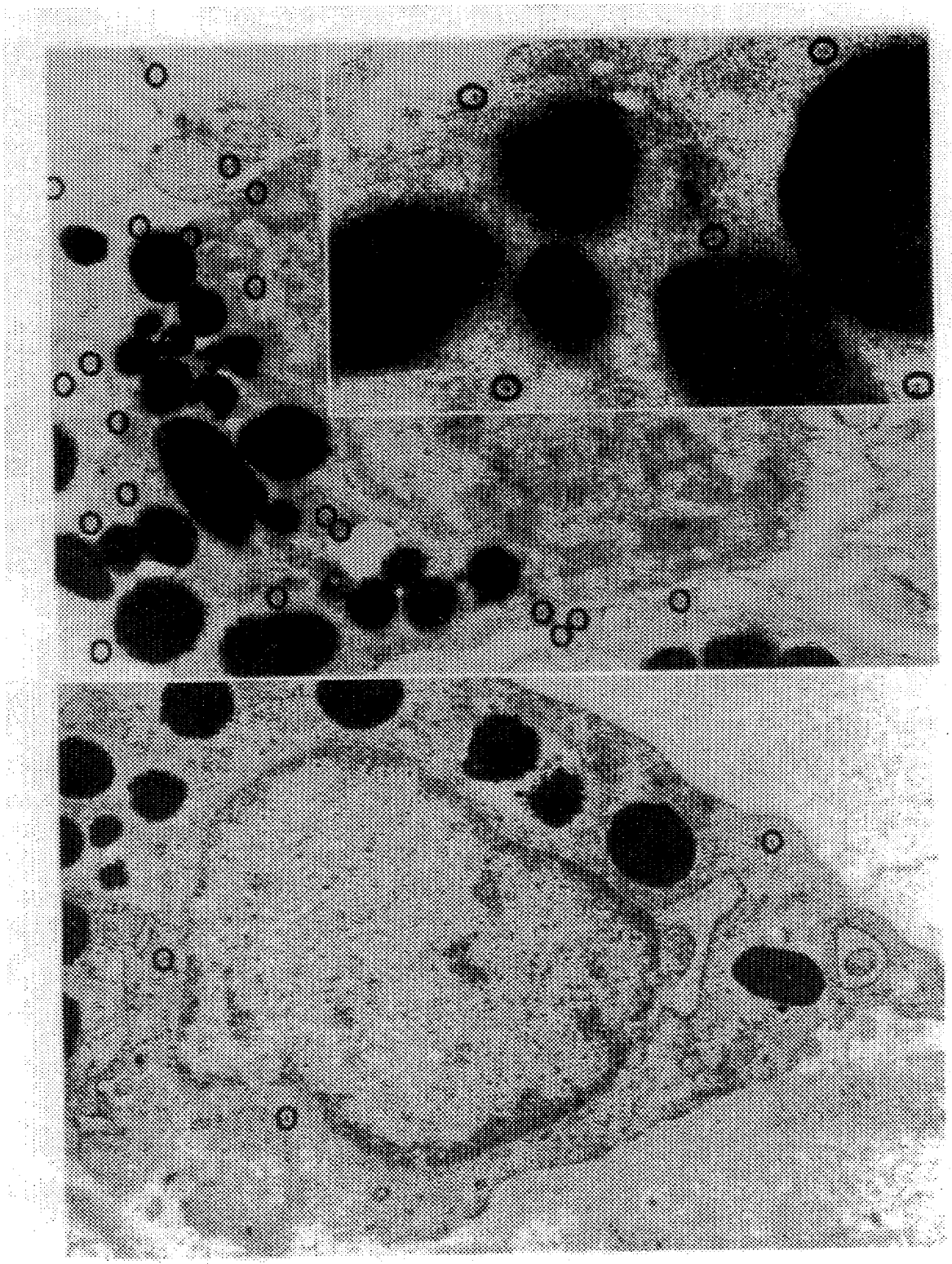
FIG. 4. Top, Labeling of melanin-containing macrophages in the trabecular meshwork in pigmentary glaucoma with anti-Mac-1 antibody and colloidal gold secondary antibody. Gold particles are circled (specimen 1362; uranyl acetate-lead citrate, X 25,000). Inset, Area of macrophages enlarged to show heavy deposition of gold particles (circled) (uranyl acetate-lead citrate, X 63,000). Bottom, Trabecular cell from the same section. Note sparse background deposition of gold particles (circled) (uranyl acetate-lead citrate, X 20,500).
Figure 5:
FIG. 5. Positive control Mouse macrophages from line known to have the Mac-1 antigen is heavily labeled with gold particles (uranyl acetate-lead citrate, X 39,000).

A striking histologic finding was the substantial number of large, pigment-filled cells within the aqueous channels, the JXT, and the SC of PG specimens. The binding of the anti-Mac-1 antibody to these cells when 1:30 and 1:60 dilutions were used resulted in either a slightly heavy or light labeling, respectively. When the 1:40 dilution was used, the large melanin-containing cells had a concentration of 27 gold particles per square micrometer, compared with 4.4 gold particles per square micrometer in the trabecular cells or in the extracellular space (FIG. 4). Positive controls, mouse macrophages known to have the Mac-1 antigen, were also well-labeled with Mac-1 antibody (FIG. 5). Thus, according to these experiments, the large pigment-laden cells can be identified as macrophages. In addition, the large size of these cells, their uniformly well-preserved structure, the nuclear chromatin pattern, and villous surface specializations are characteristic of macrophages. The positive and negative controls yielded the appropriate responses.

Figure 6:
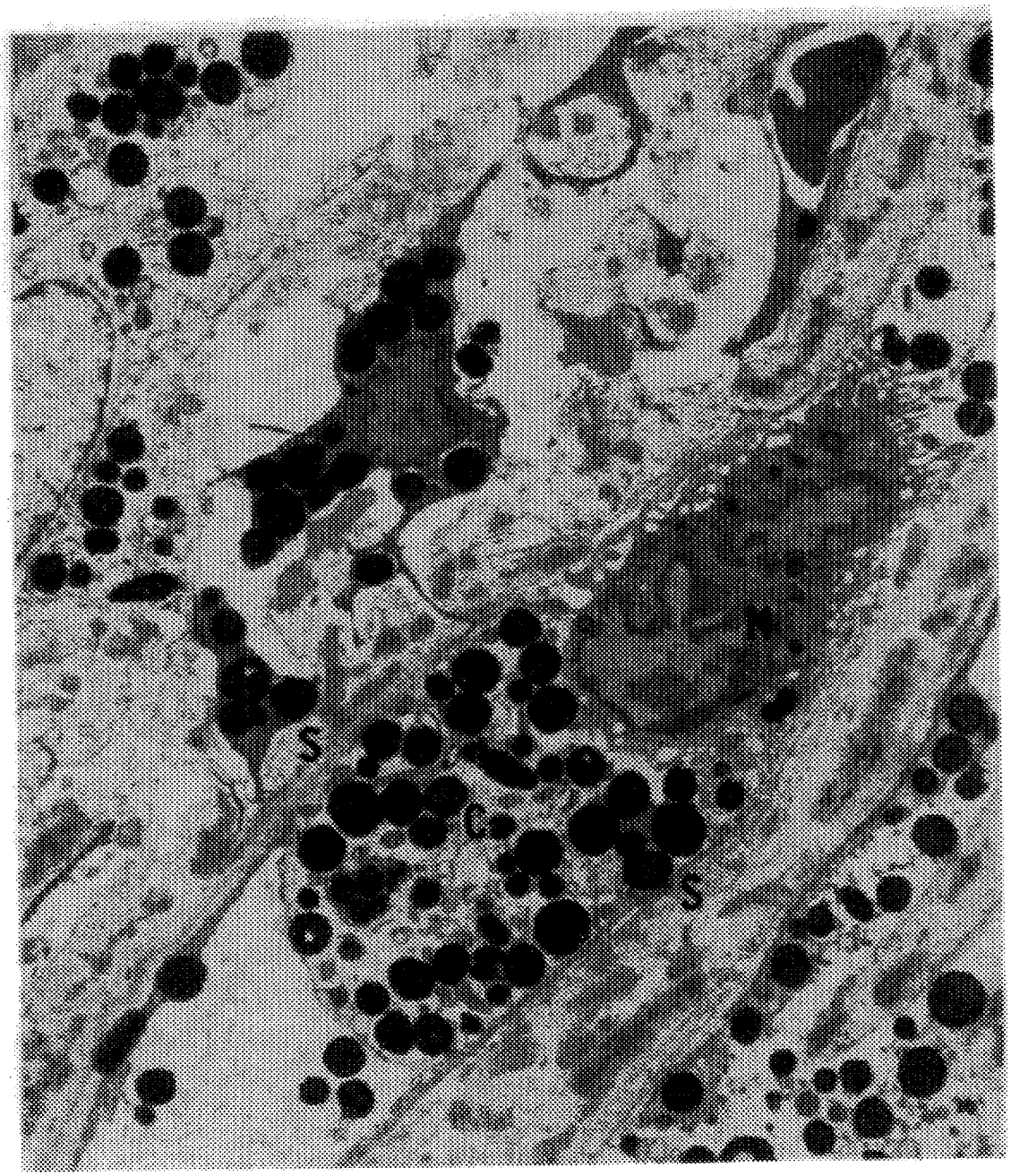
FIG. 6. Well-preserved, healthy-appearing macrophages (M) adjacent to necrotic trabecular cell (TC) disposed between adjacent trabecular sheets (S) in pigmentary glaucoma. The macrophages has abundant cytoplasmic processes and a few phagosomal inclusions. The trabecular cell has pale cytoplasm, few organelles, and abundant melanin granules (specimen 1362; uranyl acetate-lead citrate, X 2500).
Figure 7:
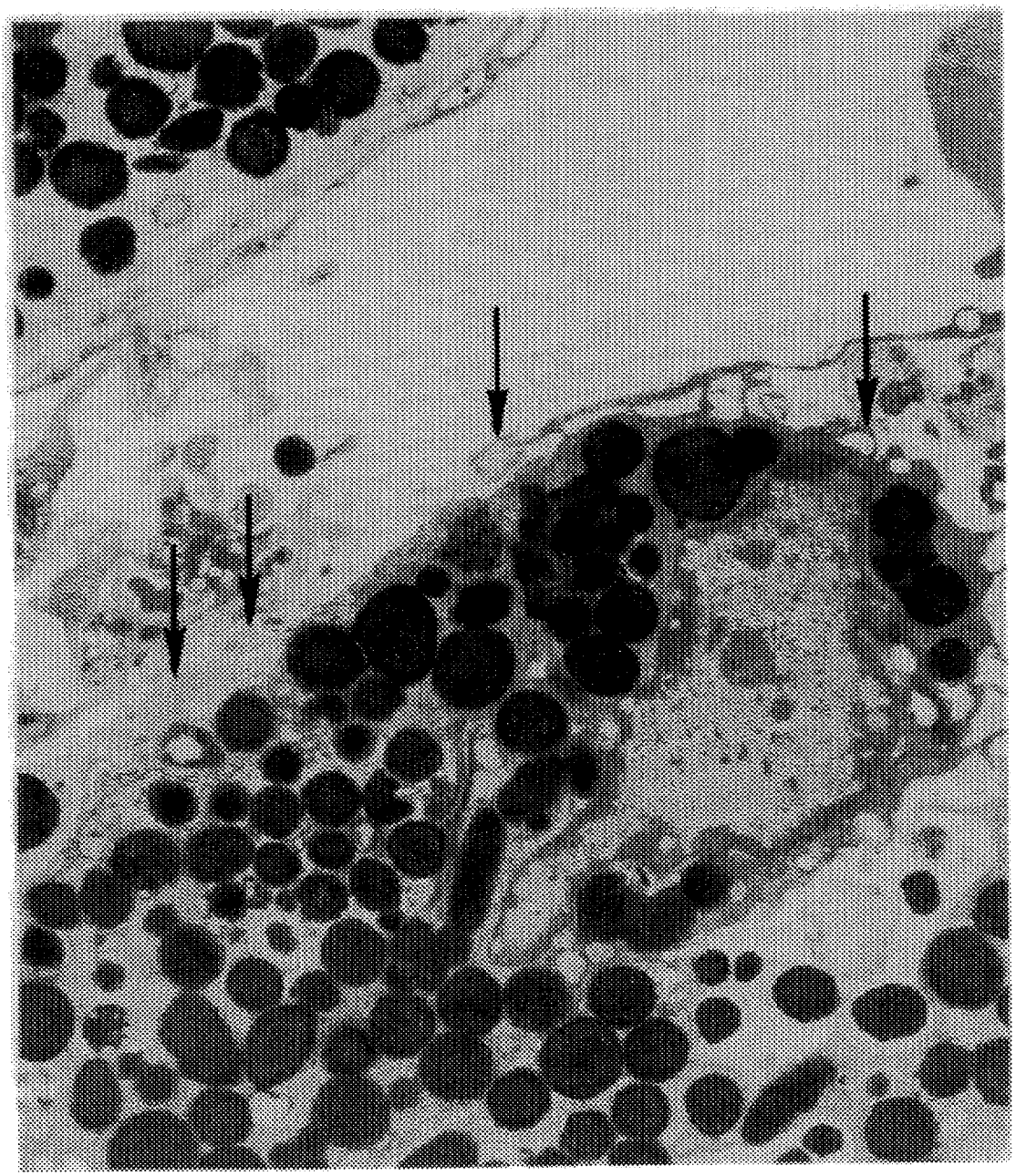
FIG. 7. Numerous melanin granules contained in a macrophages found in corneoscleral meshwork in pigmentary glaucoma. Note cytoplasmic processes (arrows) (specimen 1362; uranyl acetate-lead citrate, X 12,500).
Figure 8:
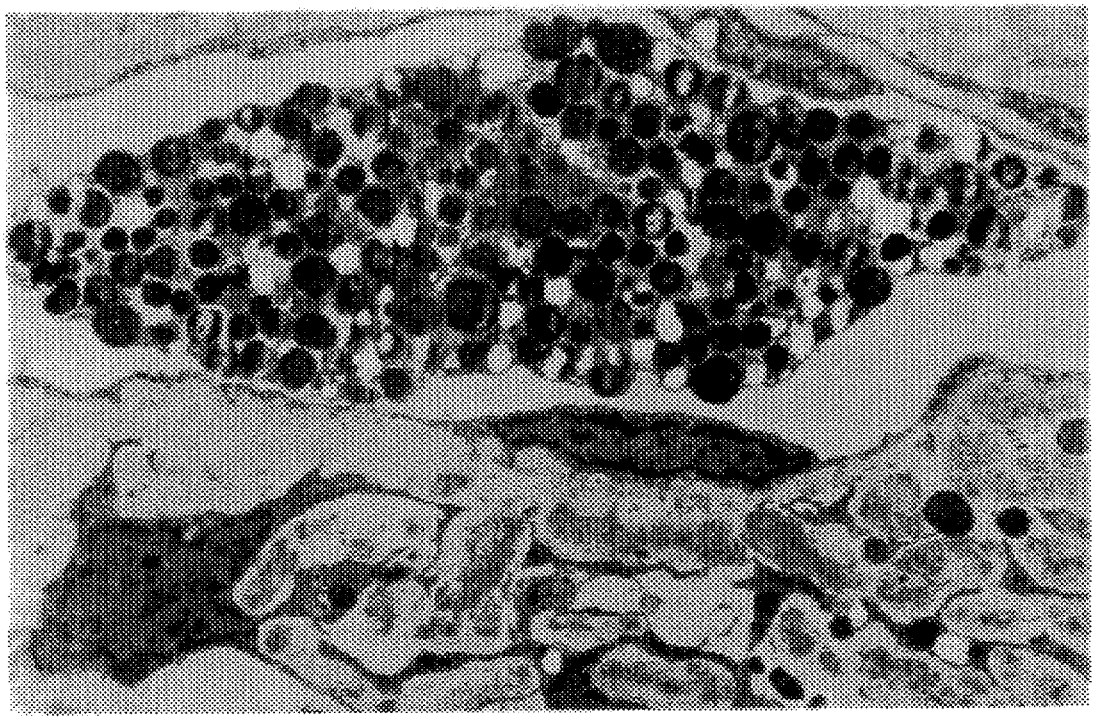
FIG. 8. Electron micrograph of the same cell as in Color FIG. 2. This presumptive macrophages is completely filled with melanin (uranyl acetate-lead citrate, X 6200).

FIGS. 2A, 2B and FIGS. 6 through 8 are images of macrophages presumably engaged in the collection and removal of the pigment from the TM tissue. The collected pigment is derived from two sources: one consists of granules released by necrotic trabecular cells and the other is aqueous borne. In FIG. 6, a macrophages containing a few intracellular melanin granules is situated between two trabecular sheets and is in direct contact with a necrotic trabecular cell and some extracellular melanin granules. In FIG. 7, another macrophages is shown that is completed filled with partially digested melanin granules. In color FIG. 2 and FIG. 8, an enormously enlarged macrophage in the lumen of SC is filled with melanin granules. Such cells can be observed in various stages of passage through the wall of SC.

Comment

The data presented support the following three new concepts: (1) that the cul-de-sacs may represent an important site of resistance to aqueous outflow in the normal TM; (2) that the smaller cul-de-sac area we calculated for the POAG and PG specimens may be sufficient to account for the major increase in resistance in the glaucomatous conditions represented; and (3) that the macrophages is the major cell type involved in the clearance of melanin from the TM in PG.

To develop the first concept, it is necessary to estimate the flow resistance generated by the cul-de-sacs. Facility (C) is calculated by multiplication of the cul-de-sac area (A) by the hydraulic conductivity ($H_c$) of the cells lining these structures: $C = A \times H_c$. Resistance (R) is by definition the inverse of facility, so that $R = 1/C$ or $1/(A \times H_c)$.

The $H_c$ of the cells lining the cul-de-sacs is unknown but may be assessed indirectly. Relevant information is available from our studies of monolayers of cultured human TM cells grown on filter supports. We monitored the $H_c$ of TM cells from 14- and 30-year-old donors for several weeks, using our published methods.[21,22] In 19 monolayers from the 14-year-old donor line, the $H_c$ measured 0.9±0.5 µL·min$^{-1}$·mm Hg$^{-1}$·cm$^{-2}$ 10 days after seeding and became progressively less resistive, so that by 17 days after seeding this value became 2.5±1.0 µL·min$^{-1}$·mm Hg$^{-1,-2}$, 4.5±3.2 µL·min$^{-1}$·mm Hg$^{-1}$·cm$^{-2}$ by 1 month after seeding, and 5.2±5.0 µL·min$^{-1}$ Hg$^{-1}$·cm$^{-2}$ by 2 months after seeding when the experiment was terminated. Ten monolayers from the 30-year-old donor line behaved in a similar fashion, as the $H_c$ measured 1.0±0.5 µL·min$^{-1}$·mm Hg$^{-1}$·cm$^{-2}$ at 10 days after seeding, increasing progressively to 3.7±1.2 µL·min$^{-1}$·mm Hg$^{-1}$·cm$^{-2}$ by 1 month after seeding and 5.3±2.2 µL·min$^{-1}$·mm Hg$^{-1}$·cm$^{-2}$ at a 1.5 months, when the experiment was terminated.

Cells that have been cultured for 1 month or longer after seeding have a structure that more closely resembles the structure of the lining trabecular cells in adult normal eyes than do cells soon after seeding. Thus, it seems reasonable to assume that the $H_c$ of the cells lining cul-de-sacs is approximately 5 or 10 µL·min$^{-1}$·mm Hg$^{-1}$·cm$^{-2}$. The cul-de-sac area is equal to 0.036 cm$^2$ according to our estimates (see the "Results" section). For the calculation of the cul-de-sac resistance using the values for square areas and an $H_c$ of 10 µL·min$^{-1}$·mm Hg$^{-1}$·cm$^2$, the resistance in normal subjects would be equal to 1/(0.036 cm$^2 \times$10 µL·min$^{-1}$·mm Hg$^{-1}$·cm$^{-2}$), or 1/0.36 or 2.8 mm Hg·µL$^{-1}$·min$^{-1}$. This value represents more than 80% of the total outflow resistance of a normal eye, which averages 3.3 mm Hg·µL$^{-1}$.[23,24] When the calculation is done for circular areas, R would be 3.7 mm Hg·µL$^{-1}$min$^{-1}$, which is slightly higher than the total resistance in normal subjects.

Some support for this novel concept has been provided in recent experiments in which the resistance at various TM sites was measured directly in vivo in the monkey eye. Maepea and Bill[25] found that "most of the resistance was located in the outer parts of the corneoscleral meshwork, the JXT and the inner wall of Schlemm's canal." Two of these three locations had been evaluated in previous morphometric studies,[7,8,26] and the third location corresponds to the cul-de-sacs. The resistance provided by SC endothelium was calculated to the 0.21 mm Hg·μL$^{-1}$·min$^{-1}$,[26] or 6% of the total normal outflow resistance. The JXT resistance has not been definitely determined; however, previous results indicate that it contributes much less than 1% of the total resistance.[7] Thus, surprisingly little resistance is accounted for by two of these three potential resistance sites. The third site, located in the outer corneoscleral meshwork, corresponds to our cul-de-sacs, and the high resistance values calculated by us are in keeping with expectations based on direct measurements reported by Maepea and Bill.[25]

The second concept is that in PG and POAG, but not in PDS, the increase in resistance is related to a 70% reduction in the area occupied by the cul-de-sacs. The cul-de-sac area in the glaucomatous specimens we studied averages 0.011 cm$^2$ using the values for squares, so that C equals 0.11 μL·min$^{-1}$·mm Hg$^{-1}$. Moreover, the calculated facility value of 0.11 μL·min$^{-1}$·mm Hg$^{-1}$ is already in the borderline glaucomatous range. For the model using circular areas, C would be 0.08 μL·min$^{-1}$·mm Hg$^{-1}$, or well within the glaucomatous range. This threefold to fourfold decrease in facility (or increase in resistance) is of the magnitude expected for an alternation that could account for the glaucomatous condition.

We propose the following sequence of events leading to the development of glaucoma in PG and POAG, and its absence in PDS. The initial event appears to be a loss of trabecular cells. The origin of cell loss in PG and PDS is most likely related to the phagocytic process and specifically to the ingestion of melanin. A phagocytic overload was shown to produce cell injury and death by Shirato et al.,[27] who reported necrosis in trabecular cells that had ingested a large number of plastic beads. Ingestion of large quantities of particulate matter results in a pronounced respiratory burst and the production of deleterious free radicals.[28-30] Phagocytosis of melanin poses a particular problem because melanoprotein is usually only partially digested and must be retained within intracellular storage vacuoles.[16] There, melanin can also generate the same reactive oxygen species.[31,32] Melanin ingestion produces a depletion of trabecular cells in in vitro experiments,[12] and decreased cellularity in our specimens is well correlated with the pronounced phagocytosis of pigment granules in the uveoscleral and corneoscleral meshwork. The origin of the loss of cells in POAG remains unknown. However, Kahn et al[33] and Polansky et al[34] have also invoked the role of free radicals in this process. The development of glaucoma follows next, as a cumulative result of several secondary alterations, culminating in sclerosis of the meshwork at large and loss of "porosity" of the uveoscleral and corneoscleral meshworks.[10,11] Cell loss leaves the trabecular sheets denuded of their cellular lining and vulnerable to fusion and obliteration of the aqueous channels. As this process continues, obstruction sites extend into the outermost structures of the corneoscleral meshwork, so that in PG and POAG, one can measure a loss of cul-de-sac area and a corresponding increased resistance to outflow. In PDS, these steps have not occurred, which implies that the secondary changes are crucial for development of the glaucomatous condition.

A third concept presented herein is that macrophages appear to be the major and perhaps the only cell type engaged in the clearance of pigment away from the TM tissues and into the circulation. Macrophages were identified by their distinct appearance and by binding studies using antimacrophages monoclonal antibodies. Unlike the trabecular cells, macrophages remain viable even after they have become enormously enlarged by the ingestion of massive amounts of pigment. Macrophages were often located adjacent to necrotic trabecular cells, where they may have migrated in response to cytokines released by the injured, pigment-filled trabecular cells.[35,37] They were also observed within the aqueous channels, between the cells of the cul-de-sacs, in the JXT, between the endothelial cells of SC, in the canal, and in the aqueous veins. This distribution is consistent with a postulated sequence of events involved in the clearance of pigment from the TM tissues. Because we observed no pigment-filled trabecular cells with a similar distribution, we believe that macrophages are primarily responsible for such pigment clearance. Although previous investigators had noticed macrophages in the TM tissues of PG specimens, they did not comment on their possible functions.[38] In agreement with these observations, experimental studies in monkeys have shown that macrophages had invaded the TM tissue 1 week after pigment infusion, but these authors emphasized the role of the trabecular cells in pigment clearance.[39] Macrophages are also recruited to the TM after laser trabeculoplasty, where they are found at the site of the laser burn (J. A. A., unpublished data, 1990). In view of the well-established role of macrophages to direct and control the wound-healing process and to act as scavengers to remove obstructing particulate matter, we are investigating the potential use of this cell type for the treatment of PG, POAG, and other glaucomas.

Our comparative study of three diagnostic groups (PG, PDS, and POAG) having cell loss as a common occurrence but with glaucoma affecting only two of these groups (PG and POAG) has allowed the identification of key alterations for progression to the glaucomatous condition. These findings provide new arguments in support of our original hypothesis that POAG is a cellular disease[9-11] and underscore the importance of cells in the regulation of aqueous outflow and in the development of glaucoma. It seems as if any process (e.g., pigment deposition, inflammation, repeated angle closure episodes, excessive laser therapy, trauma, viral and other infections) that results in the loss of trabecular cells could produce a glaucomatous condition. This study has also uncovered the participation of macrophages in the removal of pigment from the outflow pathway and has prompted us to investigate how these cells may be used in glaucoma therapy.

References

1. Murphy C. G., Johnson, M. c., Alvarado, J. A. Juxtacanalicular tissue in pigmentary and primary open-angle glaucoma: the hydrodynamic role of pigment and other constituents. *Arch Ophthalmol.* (1992) 110:1779–1785.

2. Rohen, J., Futa R., Lutjen-Drecoll, E. The fine structure of the cribriform meshwork in normal and glaucomatous eyes as seen in tangential sections. *Invest Ophthalmol Vis Sci.* (1981) 21:574–585.

3. Alvarado J., Yun A., Murphy C. Juxtacanalicular tissue in primary open-angle glaucoma and in nonglaucomatous normals. *Arch Ophthalmol.* (1986) 104:1517–1528.

4. Murphy C., Yun A., Newsome D., Alvarado J. Localization of extracellular proteins of the human trabecular meshwork by indirect immunofluorescence. *Am J Ophthalmol.* (1987) 104:33–43.

5. Lutjen-Drecoll E., Shimizu T., Rohrbach M., Rohen J. Quantitative analysis of plaque material in the inner and outer wall of Schlemm's canal in normal and glaucomatous eyes. *Exp Eye Res.* (1986) 42:443–457.

6. Goossens W., Hvizd M., Higbee R., Palmberg P., Knepper P. GAG stratification in normal and primary open-angle glaucoma juxtacanalicular connective tissue. *Invest Ophthalmol Vis Sci Suppl.* (1989) 30:205.

7. Ethier C., Kamm R., Palazewski B. Calculations of flow resistance in the juxtacanalicular meshwork. *Invest Ophthalmol Vis Sci.* (1986) 27:1741–1750.

8. Seiler T., Wollensak J. The resistance of the trabecular meshwork to aqueous humor outflow. *Graefes Arch Clin Exp Ophthalmol.* (1985) 223:88–91.

9. Alvarado J., Murphy C., Polansky J. Age-related changes in trabecular meshwork cellularity. *Invest Ophthalmol Vis Sci.* (1981) 21:714–727.

10. Alvarado J., Murphy C., Juster R. Trabecular meshwork cellularity in primary open-angle glaucoma and non-glaucomatous normals. *Ophthalmology* (1984) 91:564–579.

11. Alvarado J., Murphy C., Juster R., Polansky J. Studies on the pathogenesis of primary open-angle glaucoma: regional analyses of trabecular meshwork cellularity and dense collagen. In: Ticho U. David R., eds. *Recent Advances in Glaucoma.* New York. N.Y.: Elsevier Science Publishing Co Inc: 1984:3–8.

12. Grierson I. What is open-angle glaucoma? *Eye* (1987) 1:15–28.

13. Grierson I., Wang Q., McMenanin, Lee W. The effects of age and glaucoma medications on the meshwork cell population. *Res Clin Forums.* (1982) 4:69–92.

14. Richardson T., Hutchinson B., Grant W. the outflow tract in pigmentary glaucoma: a light and electron microscopy study. *Arch Ophthalmol.* (1977) 95:1015–1025.

15. Richardson T. Pigmentary glaucoma. In: Ritch R., Shields M. B. Krupin T, eds. *The Glaucomas.* St. Louis, Mo.: Mosby-Year Book; (1989) 981–995.

16. Rodrigues M. Spaeth G., Weinreb S., Sivalingham E. Spectrum of trabecular pigmentation in open-angle glaucoma: a clinicopathologic study. *Trans Am Acad Ophthalmol Otolaryngol.* (1976) 81:258–276.

17. Hogan M. J., Alvarado J. A., Weddell J. In: *Histology of the Human Eye: An Atlas and Textbook.* Philadelphia, Pa.: W. B. Saunders Co (1971) 154–165.

18. Springer T., Galfre G., Secher D., Milstein C. Mac-1: a macrophages differentiation antigen identified by monoclonal antibody. *Eur J Immunol.* (1979) 9:301–306.

19. Ho M-K, Springer A. Mac-1 antigen: quantitative expression in macrophages populations and tissues, and immunofluorescent localization in spleen. *J. Immunol.* (1982) 128:2281–2286.

20. McEwen W. Application of Poiseuille's law to aqueous outflow. *Arch Ophthalmol.* (1958) 60:290–294.

21. Perkins T., Alvarado J., Polansky J. Trabecular meshwork cells grown on filters: conductivity and cytochalasin effects. *Invest Ophthalmol Vis Sci.* (1988) 29:1836–1846.

22. Alvarado J. Epinephrine effects on major cell types of the aqueous outflow pathway: in vitro studies/clinical implications. *Trans Am Ophthalmol Soc.* (1990) 87:267–288.

23. Grant W. Clinical measurements of aqueous outflow. *Arch Ophthalmol.* (1951) 46:113–131.

24. Chandler P., Grant W. *Glaucoma.* Philadelphia, Pa.: Lea & Febiger (1979).

25. Maepea O., Bill A. The pressures in the episcleral veins. Schlemm's canal and the trabecular meshwork in monkeys: effects of changes in intraocular pressure. *Exp Eye Res.* (1989) 49:645–663.

26. Bill A. Svedberge B. Scanning electron microscopic studies of the trabecular meshwork and the canal of Schlemm: an attempt to localize the main resistance to outflow of aqueous humor in man. *Acta Ophthalmol.* (1972) 50:295–319.

27. Shirato S., Murphy C., Bloom E, et al. Kinetics of phagocytosis in trabecular meshwork cells: flow cytometry and morphometry. *Invest Ophthalmol Vis Sci.* (1989) 30:2499–2511.

28. Karnovsky M. L., Badwey J. A. Respiratory burst during phagocytosis: an overview. *Methods Enzymol.* (1986) 132:353–354.

29. Chakravarti B., Chakravarti D. N. Phagocytosis: an overview. *Pathol Immunopathol Res.* (1987) 6:316–342.

30. Borregaard N. The respiratory burst: an overview. In: Sbarra A. J., Strauss R. R., eds. *The Respiratory Burst and Its Physiological Significance.* New York, N.Y.: Plenum Press: 1988:1–31.

31. Cope F., Sever R., Polis B. Reversible free radical generation in the melanin granules of the eye by visible light. *Arch Biochem Biophys.* (1963) 100:171–177.

32. Ranadize N., Shirvadkar S., Persad S., Menon A. Effects of melanin-induced free radicals on the isolated rat peritoneal mast cells. *Soc Invest Dermatol.* (1986) 86:303–307.

33. Kahn M., Giblin J., Epstein D. Glutathione in calf trabecular meshwork and its relation to aqueous humor outflow facility. *Invest Ophthalmol Vis Sci.* (1983) 24:1283–1287.

34. Polansky J., Wood I., Maglio M., Alvarado J. Trabecular meshwork cell culture in glaucoma research: evaluation of biological activity and structural properties of human trabecular cells in vitro. *Ophthalmology.* (1984) 6:580–595.

35. Diegelmann R., Cohen, K., Am K. The role of macrophages in wound repair: a review. *Plast Reconstr Surg.* (1981) 68:107–113.

36. Adams D. Molecular interactions in macrophages activation. *Immunol Today.* (1989) 10:33–35.

37. Balkwill F., Burke F. The cytokine network. *Immunol Today.* (1989) 10:299–304.

38. Kampik A., Green W., Quigley H. Scanning and transmission electron microscopic studies of two cases of pigment dispersion Syndrome. *Am J Ophthalmol.* (1981) 91:573–587.

39. Epstein D. L., Freddo T. F., Anderson P. J., Patterson M. M., Bassett-chu S. Experimental obstruction to aqueous outflow by pigment particles in living monkeys. *Invest Ophthalmol Vis Sci.* (1986) 27:387–395.

Although the foregoing invention has been described in detail for purposes of clarity of understanding, it will be obvious that certain modifications may be practiced within the scope of the appended claims.

What is claimed is:

1. A method for treating glaucoma in a patient, said method comprising introducing macrophages obtained from the patient to the anterior chamber of an eye of the patient in an amount effective to lower intraocular pressure by clearance of particulate matter from and restoration of aqueous outflow through the trabecular meshwork and to lower intraocular pressure.

2. A method as in claim 1, wherein the macrophages are obtained by isolating monocytes from the patient and culturing the monocytes in vitro to produce macrophages.

3. A method as in claim 2, wherein the monocytes are obtained form peripheral blood.

4. A method for treating a condition selected from the group consisting of pigmentary glaucoma and primary open-angle glaucoma in a patient, said method comprising introducing an effective amount of macrophages obtained from the patient into the anterior chamber of the eye of the patient.

5. A method as in claim 4, wherein the macrophages are obtained by isolating monocytes from the patient and culturing the monocytes in vitro to produce macrophages.

6. A method as in claim 5, wherein the monocytes are obtained from peripheral blood.

* * * * *